United States Patent [19]

Fuchs et al.

[11] Patent Number: 5,364,954
[45] Date of Patent: Nov. 15, 1994

[54] PROCESS FOR THE PREPARATION OF DIORGANOTIN DICARBOXYLATES

[75] Inventors: Reiner Fuchs, Ober-Ramstadt; Johannes Kaufhold; Kornelia Malzacher, both of Lindenfels, all of Germany

[73] Assignee: Ciba-Geigy Corporation, Ardsley, N.Y.

[21] Appl. No.: 82,185

[22] Filed: Jun. 24, 1993

[30] Foreign Application Priority Data

Jun. 30, 1992 [CH] Switzerland ............... 2041/92-1

[51] Int. Cl.$^5$ ................................. C07F 7/22
[52] U.S. Cl. ................................... 556/90
[58] Field of Search ........................ 556/90

[56] References Cited

U.S. PATENT DOCUMENTS

| | | | |
|---|---|---|---|
| 3,522,282 | 7/1970 | Hirshman et al. | 260/429.7 |
| 4,032,552 | 6/1977 | Dworkin et al. | 260/414 |
| 5,238,605 | 8/1993 | Abeler et al. | 252/400.1 |

FOREIGN PATENT DOCUMENTS

| | | |
|---|---|---|
| 0446174 | 9/1991 | European Pat. Off. |
| 0472783 | 3/1992 | European Pat. Off. |
| 2314191 | 6/1976 | France. |
| 1908883 | 10/1969 | Germany. |
| 2303179 | 8/1973 | Germany. |
| 2626554 | 12/1976 | Germany. |
| 1246735 | 8/1967 | Netherlands. |
| 1043609 | 9/1966 | United Kingdom. |

OTHER PUBLICATIONS

Houben-Weyl, 4 Ed. Stuttgart 1978, vol. XIII/6 pp. 304-305 and 440-441.
Derwent 00347y/01 (1976).
C.A. 72(3) 12884r (1991).
C.A. 72(3) 12879t (1991).
C.A. 75(7) 49336b (1991).
Chem. Abstracts vol. 80, 1974, 4361t.

*Primary Examiner*—José G. Dees
*Assistant Examiner*—Porfirio Nazario-Gonzalez
*Attorney, Agent, or Firm*—Michele A. Kovaleski; Luther A. R. Hall

[57] ABSTRACT

The invention relates to a process for the preparation of a pulverulent diorganotin dicarboxylate, which comprises reacting a diorganotin oxide of the formula I,

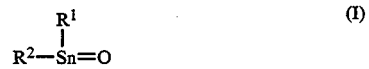

in which $R^1$ and $R^2$, independently of one another, are $C_1$-$C_8$ alkyl, at a temperature in the range from 45° C. to 70° C. in the absence of solvents and adsorbents with a dicarboxylic acid of the formula II

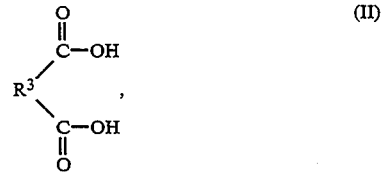

in which $R^3$ is $C_1$-$C_{18}$alkylene, cycloalkylene having 5 to 7 carbon atoms, phenylene, $C_1$-$C_{18}$alkenylene or $C_1$-$C_8$alkylene substituted by 1 or 2 hydroxyl groups, or its anhydride, and subjecting the reaction mixture and the product during the reaction and the subsequent cooling phase to constant thorough mixing. The diorganotin dicarboxylates thus obtained are suitable for the stabilization of chlorine-containing polymers against the damaging effect of light, oxygen and/or heat.

14 Claims, No Drawings

PROCESS FOR THE PREPARATION OF DIORGANOTIN DICARBOXYLATES

The invention relates to a process for the preparation of pulverulent diorganotin dicarboxylates.

The preparation of diorganotin dicarboxylates from diorganotin oxides and dicarboxylic acids or dicarboxylic anhydrides in the presence of solvents is known; cf., for example, FR-A 2 029 281, NL-A 68/18790, DE-A 1 908 883.

EP-A 446 174 teaches a solvent-free preparation process for PVC stabilisers containing diorganotin dicarboxylates in which adsorbents are added to the reaction mixture.

GB-A 1 043 609 describes the solvent-free reaction of dibutyltin oxide with maleic anhydride at 40° to 50° C, after mixing or milling the starting materials, in a reaction time of 12 hours.

According to DE-A 2 626 554, non-stoichiometric diorganotin dicarboxylate can be obtained after mixing carboxylic anhydride with an excess of diorganotin oxide in high-performance mixers, the reaction time being up to 48 hours and specific demands being made on the starting material (particle size, premixing).

These known preparation methods, which do not need additives such as solvents or adsorbents, require in part long reaction times and lead to resin-like, partly crystalline products. To prepare a commercially useful stabiliser, the products first have to be crystallised, which requires additional time, and then milled.

It has now been found that diorganotin oxides can surprisingly be reacted very rapidly with dicarboxylic anhydrides or dicarboxylic acids to give pulverulent diorganotin dicarboxylates by not exceeding in the reaction a maximum temperature of 70° C. and cooling the resulting product with constant thorough mixing. Accordingly, the invention relates to a process for the preparation of a pulverulent diorganotin dicarboxylate, which comprises reacting a diorganotin oxide of the formula I,

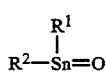

in which $R^1$ and $R^2$, independently of one another, are $C_1$–$C_{18}$alkyl, at a temperature in the range from 45° C. to 70° C. in the absence of solvents and adsorbents with a dicarboxylic acid of the formula II

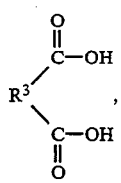

in which $R^3$ is $C_1$–$C_{18}$alkylene, cycloalkylene having 5 to 7 carbon atoms, phenylene, $C_1$–$C_{18}$alkenylene or $C_1$–$C_8$alkylene substituted by 1 or 2 hydroxyl groups, or its anhydride, and subjecting the reaction mixture and the product during the reaction and the subsequent cooling phase to constant thorough mixing.

Apart from the dialkyltin oxides mentioned, those compounds of the formula I in which $R^1$ and/or $R^2$ are $C_5$–$C_8$cycloalkyl, for example cyclopentyl, can also be used.

Preferably, the product is subjected to constant thorough mixing during the cooling phase down to 40° C.

The product of the process according to the invention is a free-flowing solid. Depending on the composition and process conditions, the particle size of the product can vary greatly, for example between a few micrometers and several millimeters, ranging, for example, from 5 μm to 5 mm, in particular ranging from 50 μm to 1 mm. In the case where a dicarboxylic acid is used in the process according to the invention, the water formed in the reaction is advantageously removed under reduced pressure, for example at 50 to 300 hPa (50 to 300 mbar). Such a process which uses a dicarboxylic acid is preferred.

The composition of the diorganotin oxides is that of the formula I. Apart from the monomers, oligomers, polymers or three-dimensional crystal lattices are also discussed as possible structures for these compounds; as to the constitution of these compounds, cf., for example, Houben-Weyl, Methoden der Organischen Chemie [Methods of Organic Chemistry], Vol. 13/6, p. 304, Thieme-Verlag, Stuttgart 1978. Hereinafter, diorganotin oxides are designated as compounds of the formula I regardless of possible deviating structures.

The diorganotin dicarboxylates formed in the reaction of diorganotin oxide with dicarboxylic acid or dicarboxylic anhydride in a molar ratio of 1:1 can be present as monomers of the formula III

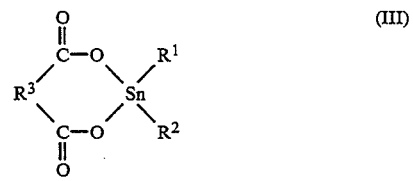

or as oligo- or polymers composed of recurring units of the formula IV

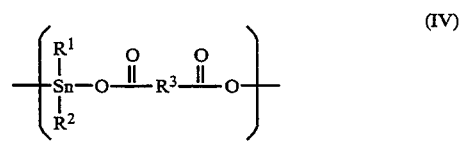

(cf., for example, R. Gächter, H. Müller, Plastics Additives Handbook, 3rd Ed., p. 285, Hanser-Verlag, Munich 1990; Houben-Weyl, Methoden der Organischen Chemie [Methods of Organic Chemistry], Vol. 13/6, p. 440, Thieme-Verlag, Stuttgart 1978).

The invention also relates to a process in which a mixture of various diorganotin oxides and/or dicarboxylic acids or dicarboxylic anhydrides is used instead of a uniform starting material of the formula I and a uniform starting material of the formula II and accordingly a mixture of various diorganotin dicarboxylates is obtained.

The process according to the invention can lead to individual compounds or else to mixtures of products.

In the process according to the invention, the starting materials can be in equivalent amounts or else in almost equivalent amounts (for example in a molar ratio of diorganotin oxide to dicarboxylic acid or dicarboxylic anhydride of 0.8:1 to 1.2:1). It is also possible to use a relatively large excess of the diorganotin oxide of the formula I. Preferably, diorganolin oxide and dicarboxylic acid or dicarboxylic anhydride are used in a molar ratio of about 1:1 to about 2:1, the tolerance being about 20%. Particular preference is given to a process in which the molar ratio is about 1:1, i.e. the organotin compound is used in 0.9 to 1.1 times the equivalent amount, relative to the dicarboxylic acid or its anhydride.

In the case where the diorganotin oxide is used in excess, the product also contains units of the formula V

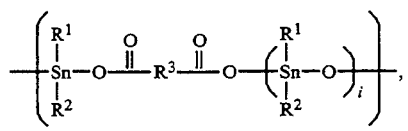

in which i is a number greater than 0, for example from the range 1 to 50.

In the case where less than the equivalent amount of diorganotin oxide is used, the product contains compounds in which only one carboxyl group of the dicarboxylic acid is esterified with the tin compound.

Examples of $R^1$ and $R^2$ as $C_1$–$C_{18}$alkyl are methyl, ethyl, propyl, isopropyl, butyl, isobutyl, tert-butyl, pentyl, hexyl, heptyl, octyl, nonyl, decyl, undecyl, dodecyl, tridecyl, tetradecyl, pentadecyl, hexadecyl, heptadecyl or octadecyl, in particular $C_1$–$C_{12}$alkyl, for example n-butyl and n-octyl.

Preferably, $R^1$ and $R^2$ are identical.

Particularly preferred diorganotin oxides are dibutyltin oxide, dioctyltin oxide and dilauryltin oxide.

Examples of suitable reactants of diorganotin oxide are the following acids or their anhydrides: maleic acid, fumaric acid, phthalic acid, 1,2-cyclohexanedicarboxylic acid, iraconic, mesaconic or glutaconic acid, malonic, succinic, isododecylsuccinic, glutaric, adipic, pimelic, suberic, sebacic, malic or tartaric acid. Maleic acid, maleic anhydride, fumaric acid, phthalic acid, phthalic anhydride, adipic, pimelic, suberic and sebacic acid are preferred; in particular maleic acid and phthalic acid and their anhydrides are preferred.

At least one of the starting materials diorganotin oxide and dicarboxylic acid or dicarboxylic anhydride is solid at the reaction temperature. Preferably, diorganotin oxide and dicarboxylic acid or dicarboxylic anhydride are solid at the reaction temperature.

In the process according to the invention a diorganotin oxide of the formula I in which $R^1$ and $R^2$, independently of one another, are $C_4$–$C_{12}$alkyl is preferably used. Particularly preferably, $R^1$ and $R^2$, independently of one another, are butyl or octyl.

The dicarboxylic acid used in the process according to the invention is preferably one of the formula II in which $R^3$ is $C_1$–$C_{18}$alkylene, o-phenylene, 1,2-cyclohexylene or one of the groups —CH=CH—,

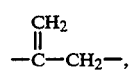

—C(CH$_3$)=CH—, —CH=CH—CH$_2$—, —CH(OH)—, —CH$_2$—CH(OH)— or —CH(OH)—CH(OH)—. Of these, all stereoisomers can be used, for example cis- or trans- —CH=CH—; (+)- or (−)-malic acid; meso-, (+)- or (−)-tartaric acid, and racemates.

The anhydride is preferably that of a dicarboxylic acid of the formula II in which $R^3$ is $C_1$–$C_3$alkylene, o-phenylene, 1,2-cyclohexylene or one of the groups cis- —CH=CH—,

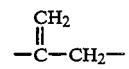

or cis- —C(CH$_3$)=CH—.

Particular preference is given to a process in which a dicarboxylic acid of the formula II is used in which $R^3$ is $C_4$–$C_8$alkylene, o-phenylene or a cis- or trans- —CH=CH— group, or the anhydride of maleic acid or phthalic is used as the anhydride of a dicarboxylic acid of the formula II.

Of very particular importance is a process in which dibutyltin oxide or diooctyltin oxide is reacted with maleic acid, phthalic acid, maleic anhydride or phthalic anhydride.

The process according to the invention is advantageously carried out in the absence of catalysts, in particular in the absence of drying agents or substances which increase the rate of the reaction and/or of the crystallisation of the product but do not have a stabilising function in chlorine-containing polymer compositions.

Particular preference is given to a process in which, apart from the starting materials of the formula I and of the formula II, no further compounds, auxiliaries or additives are used.

The process can be carded out, for example, in such a manner that the starting materials are premixed and then poured into the reactor, or the starting materials are introduced into the reactor in succession and then mixed and heated. It is also possible to operate the process continuously by introducing the starting materials continuously into the reaction zone of a suitable apparatus in suitable amounts and discharging the finished product after cooling. The requirement is that constant thorough mixing must be ensured.

Suitable apparatuses for carrying out the process are in principle all those capable of fulfilling the requirements mentioned with respect to temperature control, thorough mixing and, if desired, reduction in pressure. It is advantageous to use apparatuses which are operated continuously; of these, not only those apparatuses with uniform residence time behaviour but also those which typically result in spreading of the residence time can be used. For example, heatable mixers, driers or extruders can serve as reaction apparatuses.

Examples of mixers are forced-type mixers, V-shaped mixers, Eirich-type mixers, ploughshare mixers, plough blade mixers, paddle mixers, centrifugal screws, mixing screws, vertical screw mixers or continuous mixers. Mixers which can be evacuated are particularly preferred.

The reaction is preferably carried out in driers which advantageously can also be evacuated. Driers of this type are known per se and can be, for example, kneading driers, blade driers, trough driers, screw driers or vacuum disc driers.

As already described above, the individual components are advantageously introduced into the reaction vessel, then into the mixing device or the drying equipment in a manner appropriate to the device used. Liquid components are advantageously sprayed onto the solid component(s) by means of suitable devices.

After sufficient thorough mixing, the components are brought to the desired temperature; or, alternatively, a further component is metered to an already temperature-controlled component or mixture with sufficient thorough mixing.

The reaction of the starting materials takes place in the temperature range of 45°–70° C., preferably in the temperature range of 50°–65° C., in particular in the temperature range 60°–65° C.

The average residence time in the temperature range 45°–70° C. is advantageously 1 to 60 minutes, preferably 2 to 30 minutes.

It is preferred to apply vacuum. This vacuum is, for example, in the range from 1 to 500, preferably 10 to 500, in particular 50 to 300, especially 50 to 200, mbar.

Any water which may be formed as a reaction product is removed by the drying process initiated by increase in temperature and advantageously by reduction in pressure. It can be collected within the apparatus by condensation or discharged in the form of vapour.

After the reaction, the reaction mixture is cooled, preferably down to 40° C. or below that temperature, while constant thorough mixing is continued.

Advantageously, the total residence time of starting materials and product during the reaction and the cooling phase down to 40° C. is not more than 100 minutes. The total residence times reached are, for example 1 to 100 minutes, preferably 1 to 60 minutes, in particular 2 to 30 minutes.

Thorough mixing and cooling rate are advantageously adjusted to one another such that at no time lumps or crusts are formed on built-in parts or walls of the apparatus; advantageously, each volume portion of the mixture which is larger than the particle size of the end product comes constantly into contact with other volume portions as a result of thorough mixing.

The diorganotin dicarboxylates obtained by the process according to the invention can be used for the stabilisation of chlorine-containing polymers against the damaging effect of light, oxygen and/or heat. They are suitable, for example, for the following types of polymers: polymers of vinyl chloride, vinylic resins containing vinyl chloride units in their structure, such as copolymers of vinyl chloride and vinylesters of aliphatic acids, in particular vinyl acetate, copolymers of vinyl chloride with diene compounds and unsaturated dicarboxylic acids or anhydrides thereof, such as copolymers of vinyl chloride with diethyl maleate, diethyl fumarate or maleic anhydride, post chlorinated polymers and copolymers of vinyl chloride, copolymers of vinyl chloride and vinylidene chloride with unsaturated aldehydes, ketones and others, such as acrolein, crotonaldehyde, vinyl methyl ketone, vinyl methyl ether, vinyl isobutyl ether and the like; polymers of vinylidene chloride and copolymers thereof with vinyl chloride and other polymerisable compounds; polymers of vinyl chloroacetate and dichlorodivinyl ether; chlorinated polymers of vinyl acetate, chlorinated polymeric esters of acrylic acid and alpha-substituted acrylic acid; polymers of chlorinated styrenes, for example dichlorosytrene; chlorinated rubbers; chlorinated ethylene polymers; polymers and post chlorinated polymers of chlorobutadiene and copolymers thereof with vinyl chloride, rubber hydrochloride and chlorinated rubber hydrochloride; and mixtures of the polymers mentioned with one another.

A particularly preferred chlorine-containing polymer is polyvinyl chloride, in particular suspension polymers, emulsion polymers and bulk polymers.

Moreover, the process products can be used for further known applications of diorganotin dicarboxylates; examples which may be mentioned are the use as catalyst for the crosslinking of silicones according to DE-A 1 223 548 and the use as medicament for tumour control according to EP-A 472 783.

The solvent-tree process according to the invention has, for example, the advantages that there is no need for removal, disposal and reprocessing of solvents, and that the product can be used as stabiliser without any further processing in the form of a free-flowing solid.

The examples which follow further illustrate the process according to the invention. All parts or percentages given are by weight unless stated otherwise.

EXAMPLE 1

Preparation of dibutyltin phthalate from phthalic anhydride 1.48 kg of phthalic anhydride and 2.49 kg of dibutyltin oxide are mixed with one another, and the mixture is continuously added to a twin-screw laboratory extruder via an addition tunnel. The cylinder section consists of three heating zones and a cooling zone. The temperature of the mixture in the reaction zone is 63° C. After passing through the cooling extruder unit, the product temperature at the discharge point is 38° C. The throughput takes 35 minutes, which corresponds to an average residence time of 4.7 min. Dibutyltin phthalate (compound 1) is obtained as the end product in the form of a white free-flowing powder.

Analysis $C_{16}H_{22}O_4Sn$: calc. 29.9% Sn; found 30.0% Sn; chemical shift in $^{119}$Sn-NMR: −137.3 ppm.

EXAMPLE 2

Preparation of dioctyltin fumarate from fumaric acid

A mixture of 6.03 kg of fumaric acid and 18.76 kg of dioctyltin oxide is heated in a batchwise operating kneading drier to 60° C. under a pressure of 120 hPa (=120 mbar) and dehydrated at constant pressure and temperature for 20 minutes. The product is then cooled to room temperature while thorough mixing is continued. This gives dioctyltin fumarate (compound 2) as a granular solid.

Analysis $C_{20}H_{36}O_4Sn$: calc. 25.9% Sn; found 25.9% Sn; acid number (by titrimetry) 244.2 mg/g.

EXAMPLE 3

Static heating test of stabilised PVC 100.0 parts by weight of S-PVC (K value 60), 0.2 part by weight of montanic acid, 1.0 part by weight of glycerol monooleate and 1.6 parts by weight of the compound given in Table 1 (product from Example 1 or Example 2) are plasticised on mixing rolls at 190° C. for 5 minutes. Test specimens are punched out from the sheet thus obtained (thickness 0.2 mm) and subjected to thermal stress in a Mathis Thermo-Takter ® at 190° C. for the length of time given in Table 1. Before starting the heat treatment and at the times given, the Yellowness Index (YI) is determined by ASTM D 1925°–70. Table 1 shows the change in Yellowness Index having taken place after the test duration listed. The test documents the stabilising effect of the products of the process according to the invention.

TABLE 1

| ΔYI at | Change in Yellowness Index (ΔYI) of the test specimens after heating at 190° C. | | | |
|---|---|---|---|---|
| | Duration of heating/min | | | |
| | 5 | 10 | 15 | 20 |
| Comp. 1 | 0.8 | 4.0 | 16.0 | 42.4 |
| Comp. 2 | 4.4 | 11.1 | 23.2 | 31.4 |

EXAMPLE 4a

Preparation of dibutyltin maleate from maleic anhydride

Maleic anhydride and dibutyltin oxide are mixed with one another, and the mixture is reacted in a twin-screw laboratory extruder in accordance with Example 1. Dibutyltin maleate (compound 3) is obtained as the end product in the form of a white free-flowing powder.

EXAMPLE 4b

Preparation of dibutyltin maleate from maleic anhydride

A mixture of 2.28 kg of maleic anhydride and 5.97 kg of dibutyltin oxide is continuously added to a screw drier whose heat exchange areas consist of two heating and one cooling zone. Behind each heating zone, a suction device is present for removing any water of reaction which may be formed. The reaction mixture passes through both heating zones at an average residence time of 7.5 minutes, the temperature of the first heating zone being 68° C. and that of the second one being 63° C., and is then cooled to 25°–30° C. At the exit of the screw drier, dibutyltin maleate (compound 3), is obtained as a white free-flowing powder.

EXAMPLE 5a

Preparation of dioctyltin maleate from maleic anhydride

Maleic anhydride and dioctyltin oxide are mixed with one another, and the mixture is reacted in a twin-screw laboratory extruder in accordance with Example 1. Dioctyltin maleate (compound 4) is obtained as the end product in the form of a white free-flowing powder.

EXAMPLE 5b

Preparation of dioctyltin maleate from maleic anhydride

Maleic anhydride and dioctyltin oxide are added to a screw drier in accordance with Example 4b. At the exit, dioctyltin maleate (compound 4) is obtained as a white free-flowing powder.

EXAMPLE 5c

Preparation of dioctyltin maleate from maleic anhydride

Maleic anhydride and dioctyltin oxide are mixed with one another, and the mixture is reacted in a batchwise operating kneading drier in accordance with Example 2. Dioctyltin maleate (compound 4) is obtained as the end product in the form of a white free-flowing powder.

EXAMPLE 6a

Preparation of dioctyltin maleate from maleic acid

Maleic acid and dioctyltin oxide are mixed with one another, and the mixture is reacted in a twin-screw laboratory extruder in accordance with Example 1. Dioctyltin maleate (compound 4) is obtained as the end product in the form of a white free-flowing powder.

EXAMPLE 6b

Preparation of dioctyltin maleate from maleic acid

Maleic acid and dioctyltin oxide are added to a screw drier in accordance with Example 4b. At the exit, dioctyltin maleate (compound 4) is obtained as a white free-flowing powder.

EXAMPLE 7

Preparation of dibutyltin phthalate from phthalic anhydride

Phthalic anhydride and dibutyltin oxide are introduced into a screw drier in accordance with Example 4b. At the exit, dibutyltin phthalate (compound 1) is obtained as a white free-flowing powder.

EXAMPLE 8

Preparation of dioctyltin phthalate from phthalic acid

Phthalic acid and dioctyltin oxide are introduced into a screw drier in accordance with Example 4b. At the exit, dioctyltin phthalate (compound 5) is obtained as a white free-flowing powder.

EXAMPLE 9

Preparation of dioctyltin adipate from adipic acid

Adipic acid and dioctyltin oxide are introduced into a screw drier in accordance with Example 4b. At the exit, dioctyltin adipate (compound 6) is obtained as a white free-flowing powder.

EXAMPLE 10

Preparation of dioctyltin sebacate from sebacic acid

Sebacic acid and dioctyltin oxide are introduced into a screw drier in accordance with Example 4b. At the exit, dioctyltin sebacate (compound 7) is obtained as a white free-flowing powder.

What is claimed is:

1. A process for the preparation of a pulverulent diorganotin dicarboxylate, which comprises reacting a diorganotin oxide of the formula I,

in which $R^1$ and $R^2$, independently of one another, are $C_1$–$C_{18}$alkyl, at a temperature in the range from 45° C. to 70° C. in the absence of solvents and adsorbents with a dicarboxylic acid of the formula II

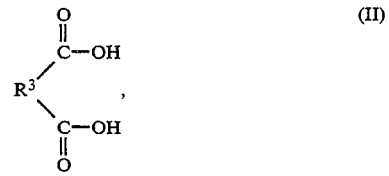

in which $R^3$ is $C_1$–$C_{18}$alkylene, cycloalkylene having 5 to 7 carbon atoms, phenylene, $C_1$–$C_{18}$alkenylene or $C_1$–$C_8$alkylene substituted by 1 or 2 hydroxyl groups, or its anhydride, and subjecting the reaction mixture and the product during the reaction and the subsequent cooling phase down to 40° C. to constant thorough mixing.

2. A process according to claim 1, wherein a diorganotin oxide of the formula I is used in which $R^1$ and $R^2$, independently of one another, are $C_4$–$C_{12}$alkyl.

3. A process according to claim 1, wherein a diorganotin oxide of the formula I is used in which $R^1$ and $R^2$, independently of one another, are butyl or octyl.

4. A process according to claim 1, wherein a dicarboxylic acid of the formula II is used in which $R^3$ is $C_1$-$C_8$alkylene, o-phenylene, 1,2-cyclohexylene or one of the groups —CH=CH—,

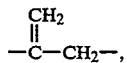

—C(CH$_3$)=CH—, —CH=CH—CH$_2$—, —CH(OH)—, —CH$_2$—CH(OH)— or —CH(OH)—CH(OH)—, or an anhydride of a dicarboxylic acid of the formula II is used in which $R^3$ is $C_1$-$C_3$alkylene, o-phenylene, 1,2-cyclohexylene or one of the groups —CH=CH—,

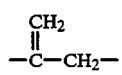

or —C(CH$_3$)=CH—.

5. A process according to claim 4, wherein a dicarboxylic acid of the formula II is used in which $R^3$ is $C_4$-$C_8$alkylene, o-phenylene, or a cis- or trans- —CH=CH— group, or the anhydride of maleic acid or phthalic acid is used as the anhydride of a dicarboxylic acid of the formula II.

6. A process according to claim 1, wherein dibutyltin oxide or dioctyltin oxide is reacted with maleic acid, phthalic acid, maleic anhydride or phthalic anhydride.

7. A process according to claim 1, wherein the reaction is carried out in a temperature range of 50°–65° C.

8. A process according to claim 7, wherein the reaction is carried out in a temperature range of 60°–65° C.

9. A process according to claim 1, wherein the total residence time of starting materials and product during the reaction and cooling phase down to 40° C. does not exceed 100 minutes.

10. A process according to claim 1, wherein, in the case where a dicarboxylic acid of the formula II is used, the water of reaction formed is removed by reducing the pressure to 50 to 300 hPa (=mbar).

11. A process according to claim 1, wherein the organotin compound is used in 0.8 to 2.2 times the equivalent amount, relative to the dicarboxylic acid or its anhydride.

12. A process according to claim 1, wherein the organotin compound is used in 0.9 to 1.1 times the equivalent amount, relative to the dicarboxylic acid or its anhydride.

13. A process according to claim 1, which is carried out in the absence of catalysts.

14. A process according to claim 1, wherein, apart from the starting materials of the formula I and of the formula II, no further compounds, auxiliaries or additives are used.

* * * * *